(12) United States Patent
Hanssen et al.

(10) Patent No.: US 10,631,769 B2
(45) Date of Patent: Apr. 28, 2020

(54) BIOSENSOR (75) Inventors: Johannes Hendrikus Leonardus Hanssen, Erlecom (NL); Robert Tweehuysen, Malden (NL)

(73) Assignee: NOVIOSENSE B.V., Nijmegen (NL)

(*) Notice: Subject to any disclaimer, the term of this patent is extended or adjusted under 35 U.S.C. 154(b) by 1044 days.

(21) Appl. No.: 14/112,095

(22) PCT Filed: Apr. 18, 2012

(86) PCT No.: PCT/EP2012/057040
§ 371 (c)(1),
(2), (4) Date: Nov. 20, 2013

(87) PCT Pub. No.: WO2012/143370
PCT Pub. Date: Oct. 26, 2012

(65) Prior Publication Data
US 2014/0081105 A1  Mar. 20, 2014

Related U.S. Application Data (60) Provisional application No. 61/517,415, filed on Apr. 18, 2011.

(51) Int. Cl.
*A61B 5/1486* (2006.01)
*G01N 27/327* (2006.01)
(Continued)

(52) U.S. Cl.
CPC .......... *A61B 5/14865* (2013.01); *C12Q 1/005* (2013.01); *C12Q 1/26* (2013.01);
(Continued)

(58) Field of Classification Search
None
See application file for complete search history.

(56) References Cited

U.S. PATENT DOCUMENTS 4,703,756 A * 11/1987 Gough ............... A61B 5/14865
128/903
5,593,852 A * 1/1997 Heller .................... C12Q 1/006
435/14
(Continued)

FOREIGN PATENT DOCUMENTS

DE    102004033288 A1 *  2/2006 ............. C08G 75/10
DE   10 2007 038 402 A1    12/2008
(Continued)

OTHER PUBLICATIONS

English Translation of DE102004033288A1.*
(Continued)

*Primary Examiner* — Etsub D Berhanu
*Assistant Examiner* — Jairo H Portillo
(74) *Attorney, Agent, or Firm* — Hudak, Shunk & Farine Co. LPA (57) ABSTRACT

A biosensor having a hollow coil having wires coiled in parallel and an electronic circuit component operably connected to the coil, wherein the wires include at least a first coiled wire which may be used as a counter electrode, a second coiled wire which may be used as a working electrode and a third coiled wire which may be used as a reference electrode, wherein the second coiled wire is provided with a biocompatible layer having a bioreceptor, wherein the electronic circuit component is capable of generating an input signal for a transceiver based upon the activity of the bioreceptor and wirelessly sending the input signal to the transceiver, wherein the electronic circuit component is encapsulated in a biocompatible resin.

17 Claims, 10 Drawing Sheets

(51) Int. Cl.
   *C12Q 1/00*   (2006.01)
   *C12Q 1/26*   (2006.01)
(52) U.S. Cl.
   CPC ... *G01N 27/3272* (2013.01); *G01N 2800/042* (2013.01); *Y10T 29/49117* (2015.01)

(56) References Cited

U.S. PATENT DOCUMENTS

| | | | | |
|---|---|---|---|---|
| 7,455,756 | B2* | 11/2008 | Choi | B82Y 30/00 204/403.01 |
| 2002/0049389 | A1* | 4/2002 | Abreu | A61B 3/1241 600/558 |
| 2002/0193611 | A1* | 12/2002 | Rajca | C07D 495/14 549/41 |
| 2007/0027370 | A1* | 2/2007 | Brauker | A61B 5/14532 600/309 |
| 2007/0142718 | A1* | 6/2007 | Abreu | A61B 3/1241 600/323 |
| 2007/0213611 | A1* | 9/2007 | Simpson | A61B 5/14532 600/365 |
| 2008/0027245 | A1* | 1/2008 | Suri | C09B 57/001 564/79 |
| 2008/0140149 | A1* | 6/2008 | John | A61N 1/0529 607/45 |
| 2008/0228047 | A1* | 9/2008 | Parks | A61B 1/00147 600/302 |
| 2009/0062634 | A1* | 3/2009 | Say | A61M 5/1723 600/347 |
| 2011/0295079 | A1* | 12/2011 | Malaurie | A61B 5/0008 600/300 |

FOREIGN PATENT DOCUMENTS

| | | |
|---|---|---|
| DE | 10 2008 049 648 A1 | 4/2010 |
| EP | 1 475 886 A1 | 11/2004 |
| WO | 2007 120442 A2 | 10/2007 |
| WO | WO 2010056624 A2 * | 5/2010 ........... A61B 5/1468 |

OTHER PUBLICATIONS lsraelachvili, Jacob. "The different faces of poly (ethylene glycol)." Proceedings of the National Academy of Sciences 94.16 (1997): 8378-8379.*

Nien, P, et al., Amperometric Glucose Biosensor Based on Entrapment of Glucose Oxidase in a Poly(3,4-entylenedioxythiophene) Film, Electroanalysis 18, 2006, No. 13-14, pp. 1408-1415.

Yu, B., et al., Coil-Type Implant Glucose Biosensor with Excess Enzyme Loading, Frontiers in Bioscience 10, 2005, pp. 512-520, XP009136935.

Kros, A, et al., Poly(3,4-ethylenedioxythiophene)-Based Copolymers for Biosensor Applications, Laboratory of Macromolecular and Organic Chemistry, 2001, pp. 738-747, XP-002361455.

Vaddiraju, S, et al., Emerging synergy between nanotechnology and implantable biosensors: A review, Biosensors and Biolectronics 25, 2010, pp. 1553-1565.

* cited by examiner

BIOSENSOR

FIELD OF THE INVENTION

The invention relates to a biosensor and to a process for the preparation thereof. The invention also relates to a medical device comprising the biosensor.

BACKGROUND OF THE INVENTION

Blood glucose monitoring is a way of testing the concentration of glucose in the blood (glycemia). It is important in the care of diabetes mellitus.

A blood glucose test is generally performed by piercing the skin (typically, on the finger tip) to draw blood, then placing the blood on a chemically active disposable strip which indicates the result either by changing colour, or changing an electrical characteristic, the latter being measured by an electronic meter.

Most people with Type 2 diabetes test at least once per day (usually before breakfast) to assess the effectiveness of their diet and exercise.

Many people with Type 2 diabetes use an oral medication to combat their insulin resistance, and test their blood glucose before and after breakfast to assess the effectiveness of their dosage. Diabetics who use insulin (all Type 1 diabetes patients and many Type 2 diabetes patients) usually test their blood sugar more often, such as 3 to 10 times per day, both to assess the effectiveness of their prior insulin dose and to help determining the time of their next insulin dose.

Improved technology for measuring blood glucose is rapidly changing the standards of care for all diabetic people. There are several methods of blood glucose testing currently available.

Chemical Test Strips: Chemical test strips are a medium cost method for monitoring blood glucose. A fairly large drop of blood, usually taken from the fingertip, is placed on a chemically prepared strip, called a blood glucose testing strip. The chemicals in the strip react with the blood, changing color according the concentration of glucose, which can then be read by comparing the color with a chart on the side of the test strip container.

Blood Glucose Meters: A blood glucose meter is an electronic device for measuring the blood glucose level. A relatively small drop of blood is placed on a disposable test strip which interfaces with a digital meter. Within several seconds, the level of blood glucose will be shown on the digital display. Sample sizes vary from 30 to 0.3 µl. Test times vary from 5 seconds to 2 minutes (modern meters are typically below 15 seconds)

Although more expensive, blood glucose meters seem a breakthrough in diabetes self care. As the drops of blood needed for the meter may be smaller, the pain associated with testing is reduced and the compliance of diabetic people to their testing regimens is improved. Although the cost of using blood glucose meters seems high; it is believed to be a cost benefit relative to the avoided medical costs of the complications of diabetes.

A recent and welcome advantage is the use of small blood drops for blood glucose testing from other places than the finger tips. This alternate site testing uses the same test strips and meter, is practically pain free, and gives the finger tips a needed break if they become sore.

A further improvement is provided by a continuous blood glucose monitor: A continuous blood glucose monitor (CGM) determines blood glucose levels on a continuous basis (every few minutes). A typical system consists of:

a) disposable glucose biosensor placed just under the skin, which is worn for a few days until replacement;

b) a link from the sensor to a non-implanted transmitter which communicates to a radio receiver;

c) an electronic receiver worn like a pager (or insulin pump) that displays blood glucose levels on a practically continuous manner, as well as monitors rising and falling trends in glycemic excursions.

Continuous blood glucose monitors measure the glucose level of interstitial fluid. Continuous monitoring allows examination of how the blood glucose level reacts to insulin, exercise, food, and other factors. The additional data can be useful for setting correct insulin dosing ratios for food intake and correction of hyperglycemia. Monitoring during periods when blood glucose levels are not typically checked (e.g. overnight) can help to identify problems in insulin dosing (such as basal levels for insulin pump users or long-acting insulin levels for patients taking injections). Monitors may also be equipped with alarms to alert patients of hyperglycemia or hypoglycemia so that a patient can take corrective action(s) (after fingerstick testing, if necessary) even in cases where they do not feel symptoms of either condition.

Studies have demonstrated that patients with continuous sensors experience less hyperglycemia and also reduce their glycosylated hemoglobin levels. This technology is an important component in the effort to develop a closed-loop system connecting real-time automatic control of an insulin pump based on immediate blood glucose data from the sensor.

SUMMARY OF THE INVENTION

It is a goal of the present invention to provide a more reliable, cheap and easy-to-use biosensor, preferably a continuous monitoring biosensor, and more preferably a bioimplant continuous monitoring biosensor. Accordingly, the present invention provides a biosensor comprising a hollow coil comprising wires coiled in parallel and an electronic circuit component operably connected to the coil, wherein the wires include at least a first coiled wire which may be used as a counter electrode, a second coiled wire which may be used as a working electrode and a third coiled wire which may be used as a reference electrode, wherein the second coiled wire is provided with a biocompatible layer comprising a bioreceptor, wherein the electronic circuit component is capable of generating an input signal for a transceiver based upon the activity of the bioreceptor and wirelessly sending the input signal to the transceiver and wherein the electronic circuit component is encapsulated in a biocompatible resin.

The sensor according to the present invention has a generally cylindrical shape and essentially consists of two components: a hollow coil and an electronic circuit component attached to the coil. The electronic circuit component is connected to the coiled wires at its relevant points. The electronic circuit component is preferably attached at the end of the coil. The electronic circuit component may be placed inside the coil or outside the coil. In the cases where the circuit component is placed outside the coil, the circuit component preferably extends in the axis direction of the coil so that the diameter of the sensor is not substantially increased by the circuit component protruding from the sensor in the radius direction. As used herein, the diameter of the sensor is understood as the largest dimension of the sensor perpendicular to the axis direction of the coil. Pref- erably, the sensor has a diameter of 0.1 to 3 mm. Preferably, the sensor has a length of 5 to 20 mm. As used herein, the length of the sensor is understood as the dimension of the total of the coil and the electronic circuit component in the axis direction of the coil.

As used herein, the term 'hollow coil' is understood to be an empty tubular body defined by one or more wires that loop around the circumference of the body, i.e. the wires are not wound around another electrode, a mandrel or other elements.

The hollow coil is advantageous in that the sensor is flexible and can follow the shape of the surrounding environment in which the sensor is placed.

During use, the sensor is placed in an aqueous environment containing a biomarker which interacts with the bioreceptor in the sensor. The aqueous environment may e.g. be the vascular system, the urinary tract, or other places in the body for instance intra-abdominal or intra-articular, intracapsular or intra-ocular. In particular, the sensor according to the invention can be worn under the upper or the lower eye lid in order to conveniently permit self monitoring of glucose levels in the lacrimal fluid and therewith give an indication of glucose levels in the blood. A sensor according to the invention suitable for use in this environment comprises glucose oxidase as the bioreceptor.

Glucose oxidase catalyzes the following reaction:

The amount of $H_2O_2$ generated is an indication of the amount of glucose in the tear liquid. For operation of the sensor, a wireless transceiver which generates an electromagnetic field is placed close to the eye. The field powers the sensor inductively. The concentration of glucose is measured potentiometrically. The electronic circuit component generates an input signal indicating the amount of glucose present in the tear liquid and transmits the signal to the transceiver.

The electronic circuit component capable of such actions is known per se and examples of such electronic circuit component is described elsewhere in the description referring to figures. More details of examples of such electronic circuit components can be found in DE 10 2007 038 402, DE 10 2008 049 648 A1 and EP 1 475 886 B1.

The biocompatible layer prevents the bioreceptor from leaking or from being degraded by e.g. proteases present in the liquid environment.

The biocompatible layer comprises the bioreceptor, i.e. the bioreceptor is immobilized in or on the biocompatible layer by being contained in, covered by or attached to the biocompatible layer. The biocompatible layer may be formed from a solution (e.g. buffer solution such as phosphate buffered saline) comprising a monomer and the bioreceptor, which is polymerized on the coil to be used as a working electrode. The biocompatible layer may also be formed by a standard dip coating process. The dip coating may be done in one step or in more than one step. When this is done in two steps, the second coil is for example immersed in a solution comprising a polymer without the bioreceptor and then is subsequently immersed in a solution comprising a polymer and the bioreceptor. In another example of a two step dip coating process, the second coil is immersed in an aqueous solution comprising the bioreceptor and then is subsequently immersed in a solution comprising a polymer for forming the biocompatible layer.

The materials used for forming the biocompatible layer may render the biocompatible layer electroconductive or non-electroconductive. The solution for forming the biocompatible layer may comprise additives e.g. to enhance the solubility, to enhance uniformity of the coating formed or to increase the conductive property of the solution or the coating formed. For example, a substituted dextran such as diethylaminoethyl-dextran (DEAE) has been shown to increase the stability of bioreceptors in the sensor. Examples of the additive for enhancing the conductive property include linear or cyclic aliphatic polyethers or polystyrenesulphonates. An example of surfactants includes polyethylene glycol (PEG).

The circuit component is embedded in a biocompatible resin capping. The resin protects the circuit component from the external environment. Examples of the resin include UV curable medical adhesives such as cyano acrylates, acrylated urethanes and silicones. The other end of the coil may also be provided with the resin capping.

The second coiled wire is arranged to allow passing of electric current generated by the activity of the bioreceptor.

One embodiment in which this is achieved is a sensor according to the invention wherein the second coiled wire has a Pt surface. This is advantageous in that a wide choice of materials is allowed for the coatings provided thereon. $H_2O_2$ decomposes into water and oxygen on the platinum working electrode. The electrochemical decomposition is measured potentiometrically.

A further embodiment in which this is achieved is a sensor according to the invention wherein the biocompatible layer comprising the bioreceptor is electroconductive. The electrons generated by the decomposition of $H_2O_2$ are passed to the second coiled wire via the electroconductive layer in which the bioreceptor is present. In this case, the second coiled wire may be any electrode material for example those having a surface of Pt, Pd or an alloy thereof.

The surface of the coiled wires may be made of a different material from the inside of the wires or the same material may be used for the surface and the inside of the coiled wires. For example, the coiled wires may be made of stainless steel on which other metals such as Pt, Pd and Ag are coated.

Preferably, the coil is encapsulated in a top layer of a biocompatible material. The top layer encloses the coil when the coil is placed in a wet environment. This additional layer further increases the suitability of the use of the biosensor in a sensitive human body such as under the eyelid In preferred embodiments, the biocompatible layer comprising the bioreceptor is electroconductive and the coil is encapsulated in a top layer of a biocompatible material.

The following specific embodiments of the sensor according to the present invention are mentioned:

the second coiled wire has a Pt surface, the biocompatible layer comprising the bioreceptor is electroconductive and the coil is encapsulated in a top layer of a biocompatible material;

the second coiled wire has a Pt surface, the biocompatible layer comprising the bioreceptor is electroconductive and the coil is not encapsulated in a top layer of a biocompatible material;

the second coiled wire has a Pt surface, the biocompatible layer comprising the bioreceptor is not electroconductive and the coil is encapsulated in a top layer of a biocompatible material;

the second coiled wire has a Pt surface, the biocompatible layer comprising the bioreceptor is not electroconductive and the coil is not encapsulated in a top layer of a biocompatible material;

the second coiled wire has a surface made of a non-Pt metal, the biocompatible layer comprising the bioreceptor is electroconductive and the coil is encapsulated in a top layer of a biocompatible material and the second coiled wire has a surface made of a non-Pt metal, the biocompatible layer comprising the bioreceptor is electroconductive and the coil is not encapsulated in a top layer of a biocompatible material.

According to the present invention, only the coil may be encapsulated in the top layer or the sensor (the coil and the electronic circuit component) may be encapsulated in the top layer.

The biocompatible material used for the top layer may be any known suitable material, as long as it is permeable to the biomarker that interacts with the bioreceptor in the sensor according to the present invention.

Preferably, the biocompatible material of the top layer is a hydrophilic material. Preferably, the biocompatible material is a biocompatible hydrogel.

In some embodiments, the hydrogel is preferably a copolymer of a hydrophobic reactive monomer and a hydrophilic reactive monomer. Suitable examples may be the following combinations of hydrophilic and hydrophobic monomeric building blocks: (i) hydrophilic: N-vinylpyrrolidinone, hydrophobic: n-butylmetha-crylate; (ii), hydrophilic: hydroxyethylmethacrylate, hydrophobic: methylmethacrylate; (iii), hydrophilic: N-dimethylaminoethylmethacrylate, hydrophobic: cyclohexylacrylate.

In some embodiments, the hydrogel is a polysaccharide, for example those based on hyularon or chitosan and those based on synthetic polysaccharides such as cellulose ethylsulphonate or carboxymethylcellulose or mixtures thereof.

In some embodiments, the hydrogel is a block copolymer of polyethers differing by at least one carbon in the aliphatic region e.g. an ABA block co-polymer of polyethylene glycol and polypropylene glycol.

In some embodiments, the hydrogel is nafion (tetrafluoroethylene-perfluoro-3,6-dioxa-4-methyl-7-octenesulfonic acid copolymer).

The electroconductive polymer in the biocompatible layer comprising the bioreceptor is preferably a polymer synthesised from an optionally substituted five-membered heterocycle of formula (I)

(I)

wherein $R^1$ stands for a hetero atom, preferably N, S or O, wherein $R^2$, $R^3$ are each independently selected from the group of H, optionally substituted alkyl of preferably 1 to 4 C atoms, wherein the alkyl may be substituted with for example a hydroxyl group, alkyl group and alkyl ether, optionally substituted o-alkyl, and wherein $R^2$ and $R^3$ may form a ring together with the carbon atoms to which they are connected.

Examples of substituted 5 membered heterocycles where the hetero atom is sulphur is 3,4-alkylenedioxythiophene. Preferred examples of 3,4-alkylenedioxythiophene include 2,3-dihydrothieno[3,4-b][1,4]dioxine 3,4-dihydro-2H-thieno[3,4-b][1,4]dioxepine or 2,3,4,5-tetrahydrothieno[3,4-b][1,4]dioxocine. Other preferred examples of 3,4-alkylenedioxythiophene include 2,3-disubstituted-2,3-dihydrothieno [3,4-b][1,4]dioxine 2-substituted-2,3-dihydrothieno[3,4-b][1,4]dioxine 3-substituted-3,4-dihydro-2H-thieno[3,4-b][1,4]dioxepine 3,3-disubstituted-3,4-dihydro-2H-thieno[3,4-b][1,4]dioxepine 3,3-bis(substituted)-3,4-dihydro-2H-thieno[3,4-b][1,4]dioxepine or a 2,3,4,5-tetrasubstituted-2,3,4,5-tetrahydrothieno[3,4-b][1,4]dioxocine Particularly preferred are 2,3-dimethyl-2,3-dihydrothieno[3,4-b][1,4]dioxine 3,3-dimethyl-3,4-dihydro-2H-thieno[3,4-b][1,4]dioxepine 3,3-bis(methoxymethyl)-3,4-dihydro-2H-thieno[3,4-b][1,4]dioxepine 2,3,4,5-tetramethyl-2,3,4,5-tetrahydrothieno[3,4-b][1,4]dioxocine 2,3-dihydrothieno[3,4-b][1,4]dioxin-2-ol 2-methyl-2,3-dihydrothieno[3,4-b][1,4]dioxine 2,3-dihydrothieno[3,4-b][1,4]dioxin-2-ylmethanol 2-phenyl-2,3-dihydrothieno[3,4-b][1,4]dioxine Sodium 4-(2,3-dihydrothieno[3,4-b][1,4]dioxin-2-ylmethoxy)butane-1-sulfonate 3-methyl-3,4-dihydro-2H-thieno[3,4-b][1,4]dioxepine 3,4-dihydro-2H-thieno[3,4-b][1,4]dioxepin-3-ylmethanol 3,4-dihydro-2H-thieno[3,4-b][1,4]dioxepin-3-ol 5,10-dihydrothieno[3,4-c][2,5]benzodioxocine or 2-methyl-2,3-dihydrothieno[3,4-b][1,4]dioxine. Most preferred monomer is the unsubstituted 3,4-ethylenedioxythiophene.

Examples of the non-electroconductive material used for the biocompatible layer comprising the bioreceptor include 3,4-dihydroxy-L-phenylalanine (L-DOPA), chitosan, Nafion (tetrafluoroethylene-perfluoro-3,6-dioxa-4-methyl-7-octenesulfonic acid copolymer).

Preferably, the third coiled wire is a silver/silver chloride reference electrode. The reference electrode may also function as an antenna by being connected to the relevant points of the electronic circuit component.

The parallel wires of the sensor according to the present invention may further include a fourth coiled wire comprising an insulating layer which may be used as an antenna and/or a fifth coiled wire comprising an insulating layer which may be used as a spacer. The wires of the sensor according to the present invention may also include more than one of the further coiled wires which work as an antenna or a spacer. The insulating layer may e.g. be made of parylene, polytetrafluoro ethylene, fluorinated ethylene propylene, perfluoroxalkoxy copolymer, polyphenylene sulfide, polyether block amide, Polyether ketone, poly amide, polyimide, polyesterimide, polyethylene such as high-density polyethylene and low-density polyethylene, polyvinylidene fluoride, or a polyurethane.

The parallel wires of the sensor according to the present invention may include a further coiled wire provided with a biocompatible layer comprising a bioreceptor, which may be used as a further working electrode. The further coiled wire may have the same construction as the second coiled wire. The further coiled wire may also have a different construction from the second coiled wire, as long as it can work as a working electrode by suitable connection to the electronic circuit component. In particular, the bioreceptors on different working electrodes may be different. The coil of the sensor according to the present invention may also comprise more than one further coiled wire which work as a further working electrode.

The bioreceptor in the sensor according to the present invention is preferably an oxidoreductase, i.e. a redox enzyme. Preferably, the bioreceptor is an oxidoreductase of the enzyme commission groups EC 1.X.3 where X=1-17. Examples of the oxidoreductase of this type include EC1.1.3 (e.g. Glucose oxidase, L-gulonolactone oxidase, Thiamine oxidase, Xanthine oxidase), EC 1.3.3 (e.g. Protoporphyrinogen oxidase), EC 1.4.3 (e.g. Monoamine oxidase), EC 1.5.3 (e.g. Sarcosine oxidase, Dihydrobenzophenanthridine oxidase), EC 1.7.3 (e.g. Urate oxidase), EC 1.8.3 (e.g. Sulfite oxidase), EC 1.9.3 (e.g. Cytochrome c oxidase), EC 1.10.3 (e.g. Catechol oxidase, Laccase) and EC 1.16.3 (e.g. Ceruloplasmin).

The bioreceptor may preferably be chosen from the group consisting of glucose oxidase, lactate dehydrogenase, pyruvate dehyrrogenase and pyruvate oxidase.

According to a further aspect of the present invention, the present invention provides a medical device comprising the sensor according to the present invention and the transceiver.

According to a further aspect of the present invention, the present invention provides a process for making the sensor according to the present invention, comprising the steps of:
1) providing the hollow coil,
2) connecting the coil with the electric circuit component and
3) encapsulating the electric circuit component with a biocompatible resin.

Preferably, the process further comprises the step of 4) providing the top layer on the coil or on the coil and the electric circuit component after step 3).

According to a further aspect of the present invention, the present invention provides use of the sensor according to the present invention or the medical device according to the present invention for the measurement of glucose levels in the eye.

According to a further aspect of the present invention, the present invention provides a method for diagnosing diabetes by using the sensor according to the present invention or the medical device according to the present invention.

BRIEF DESCRIPTION OF THE DRAWINGS

The invention will be described in detail below referring to the drawings in which.

DETAILED DESCRIPTION OF THE INVENTION

Figure 1:
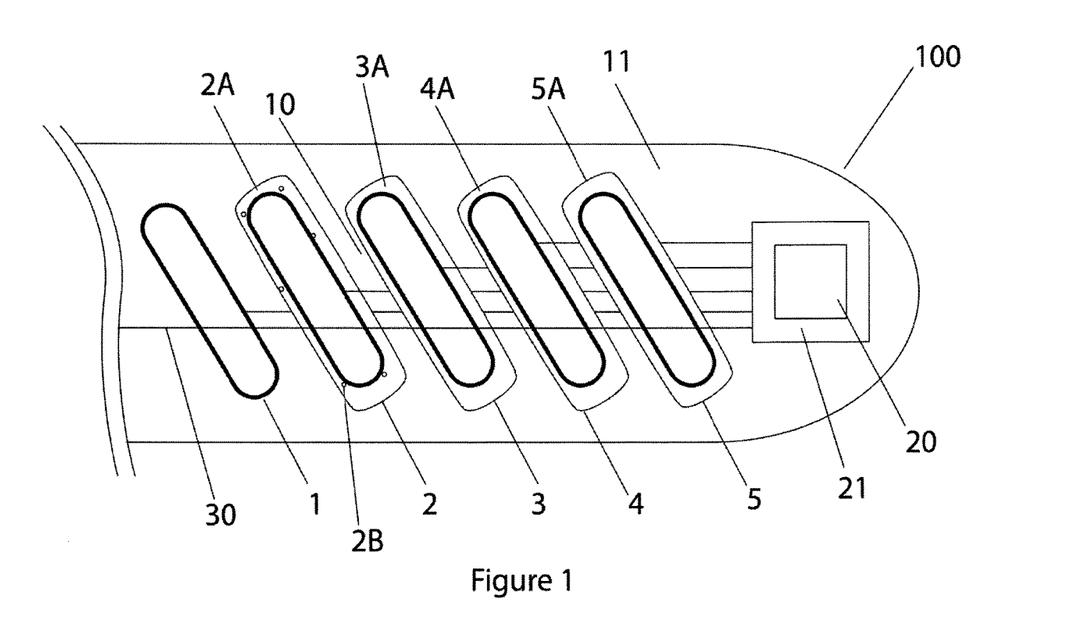
FIG. 1 schematically illustrates an embodiment of the sensor according to the invention.

FIG. 1 illustrates an embodiment of the sensor 100 according to the present invention. The sensor 100 comprises a hollow coil 10 comprising a first coiled wire 1, a second coiled wire 2, a third coiled wire 3, a fourth coiled wire 4 and a fifth coiled wire 5 coiled in parallel. The hollow coil 10 is connected to an electronic circuit 20. The electronic circuit 20 is attached at the end of the coil 10. The hollow coil 10 in this example has a diameter of 1 mm.

The first coiled wire 1 functions as a counter electrode. The second coiled wire 2 functions as a working electrode. The third coiled wire 3 functions as a reference electrode. The fourth coiled wire 4 functions as an antenna. The fifth coiled wire 5 functions as a spacer.

The hollow coil 10 and the electronic circuit 20 are covered in a continuous top layer 11. The electronic circuit 20 is embedded in a resin layer 21 under the top layer 11.

The first coiled wire 1 is made of a platinum-plated stainless steel and is provided only with the top layer 11.

The second coiled wire 2 is made of a platinum-plated stainless steel and is provided with a polymer layer 2A under the top layer 11. The polymer layer 2A is electron conductive and comprises a bioreceptor 2B, glucose oxidase in this example.

The third coiled wire 3 is a silver plated stainless steel and is coated with a silver chloride layer 3A under the top layer 11.

The fourth coiled wire 4 is made of a stainless steel and is coated with an insulating layer 4A under the top layer 11. The insulating layer 4A is made of e.g. PTFE.

The fifth coiled wire 5 is made of a stainless steel and is coated with an insulating layer 5A under the top layer 11. The insulating layer 5A is made of e.g. PTFE.

A return wire 22 for the antenna 4 extends from the electronic circuit component 2 to a different loop (not shown) of the fourth coiled wire 4, so that a closed loop antenna is formed.

During use, the sensor of this embodiment is placed in the lower eyelid filled with a tear fluid. Glucose in the tear liquid produces $H_2O_2$ by the catalytic function of glucose oxidase in the polymer layer 2A of the second coiled wire 2.

The sensor operates by an electromagnetic field generated by a transceiver (not shown) placed close to the lower eyelid. The electromagnetic field induces an electric current through the coil. The level of the electric current depends on the level of $H_2O_2$ which in turn depends on the level of glucose in the tear liquid. The electronic circuit 20 generates a signal indicating the level of glucose and sends it to the external device through coil 4.

Figure 2:
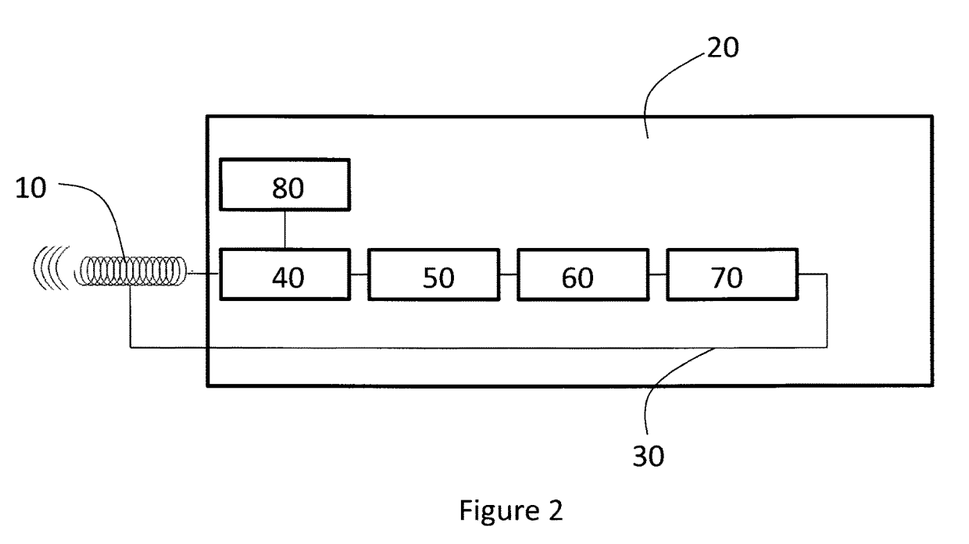
FIG. 2 is a schematic diagram of an embodiment of the sensor according to the invention in which the details of the electronic circuit component are shown.

FIG. 2 schematically illustrates an embodiment of the sensor according to the invention. The electronic circuit 20 component is illustrated more in detail. In this example, the coil 10 comprises a coiled wire used as an antenna. The electronic circuit component 20 consists of a potentiostat 40, a reference source 80, an A/D converter 50, a microprocessor 60 and a RF transceiver 70. The potentiostat 40 translates the current of the working electrode into a voltage. This voltage is digitized by the A/D converter 50 into counts. The reference source 80 provides necessary bias voltages to the potentiostat 40. The microprocessor 60 controls the processing of the sensor. The counts, i.e. the sensor raw data, are converted into a transmit data packet, for example as described in the Norm ISO 18000-3, by the microprocessor 60. The RF transceiver 70 is wirelessly connected to a reader unit (not shown here) using inductive coupling. The RF transceiver 70 is connected to the antenna coil by a return wire 30. The RF transceiver 70 transmits the data packet containing the sensor raw data to the reader unit using the antenna coil. The sensor is wirelessly powered also using inductive coupling. For data and power transmission the same antenna coil is used.

Figure 3:
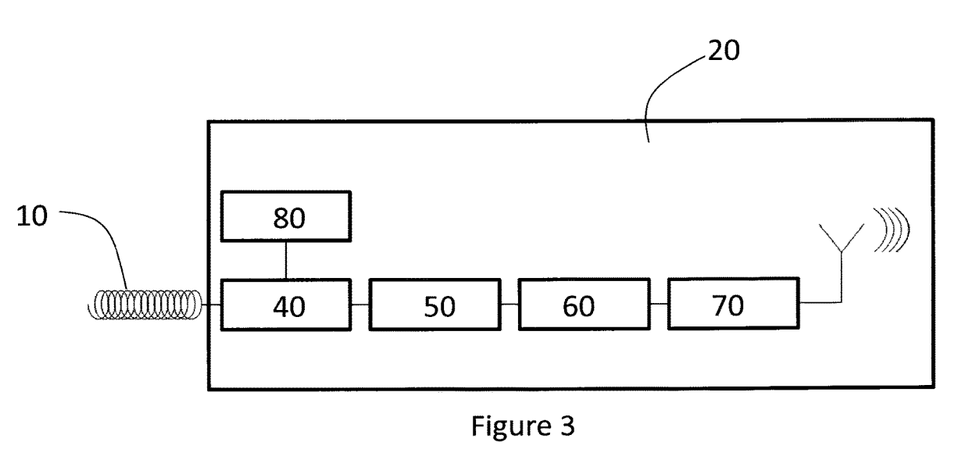
FIG. 3 is a schematic diagram of a further embodiment of the sensor according to the invention in which the details of the electronic circuit component are shown.

FIG. 3 schematically illustrates an embodiment of the electronic circuit component of the sensor according to the invention. FIG. 3 is identical to FIG. 2 except for that the antenna. In this example, the coil does not comprise a coiled wire used as an antenna. Instead, the electronic circuit component comprises an antenna for the data and power transmission.

Figure 4:
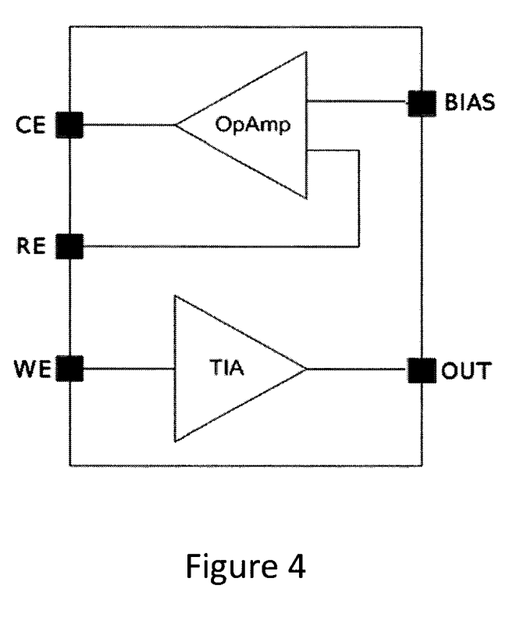
FIG. 4 illustrates the working principle of the potentiostat in the electronic circuit component in the sensor according to the present invention.

FIG. 4 illustrates the working principle of the potentiostat in the electronic circuit component in the sensor according to the present invention. The potentiostat consists of a differential input amplifier (OpAmp) and a transimpedance amplifier (TIA). The differential input amplifier compares the potential between the working (WE) and reference (RE) electrodes to adjust the required working bias potential. For this purpose, the voltage between the working and the reference electrodes may be amplified and applied to the counter electrode as an error signal. Thus the voltage between working and reference electrodes is maintained to be constant. The transimpedance amplifier is connected to the working electrode and converts the cell current into a voltage (Out). The transimpedance amplifier keeps the potential of the working electrode at virtual ground.

FIGS. 5-8 illustrate various examples of the configuration of the biosensor according to the present invention.

Figure 5:
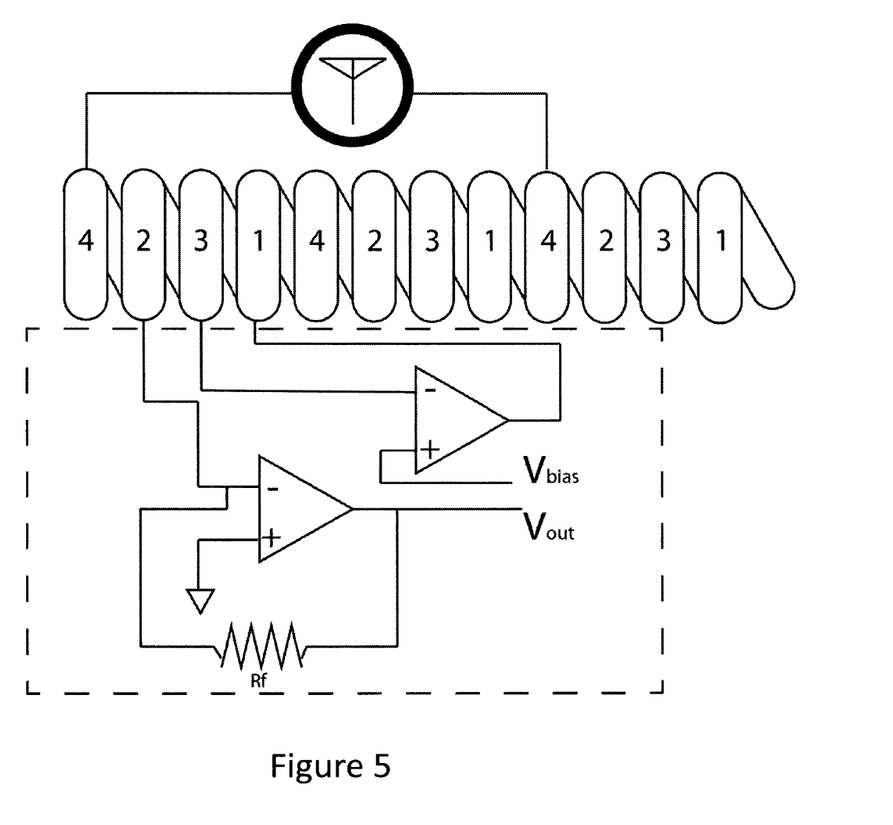
FIGS. 5-8 illustrate various examples of the configuration of the biosensor according to the present invention.

In FIG. 5, the coil consists of four wires coiled in parallel. The wires are connected to the respective points of the electronic circuit component so that they respectively function as: counter electrode 1, working electrode 2, reference electrode 3 and antenna 4.

Figure 6:
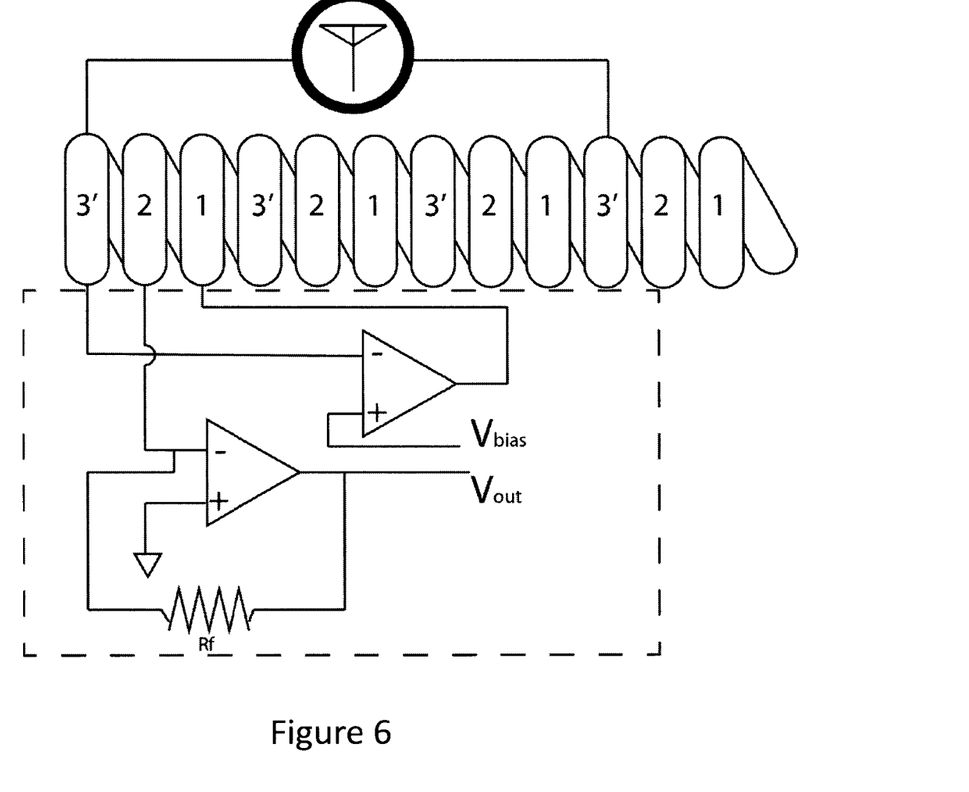

In FIG. 6, the coil consists of three wires coiled in parallel. The wires are connected to the respective points of the electronic circuit component so that they respectively function as: counter electrode 1, working electrode 2, reference electrode 3'. In this embodiment, the wire which functions as a reference electrode also functions as an antenna.

Figure 7:
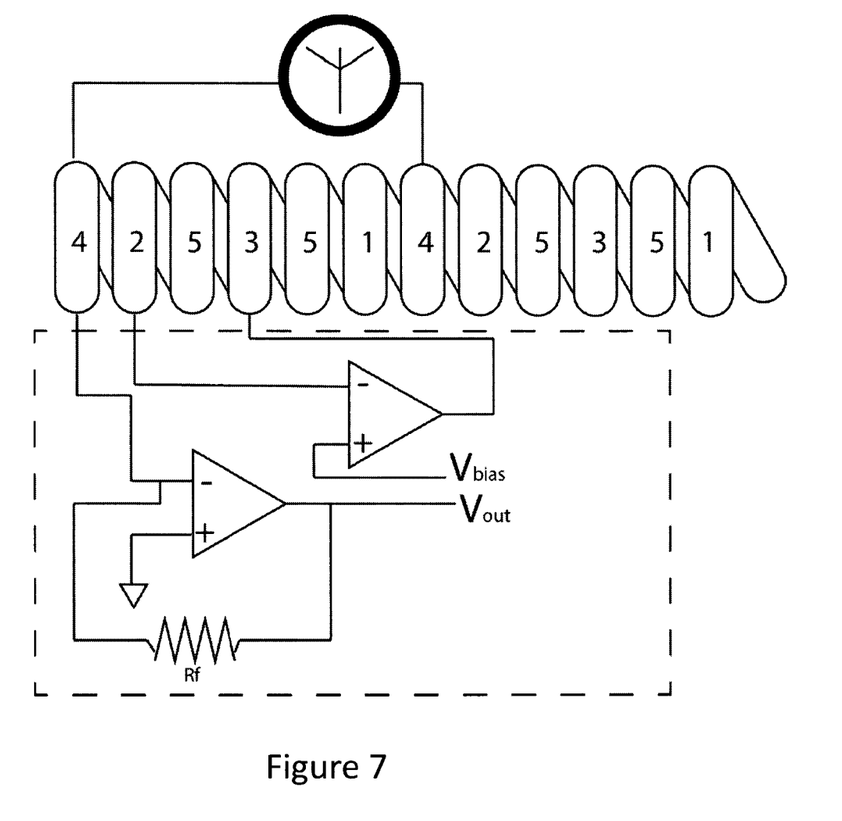

In FIG. 7, the coil consists of five wires coiled in parallel. The wires are connected to the respective points of the electronic circuit component so that they respectively function as: counter electrode 1, working electrode 2, reference electrode 3, antenna 4 and spacer 5.

Figure 8:
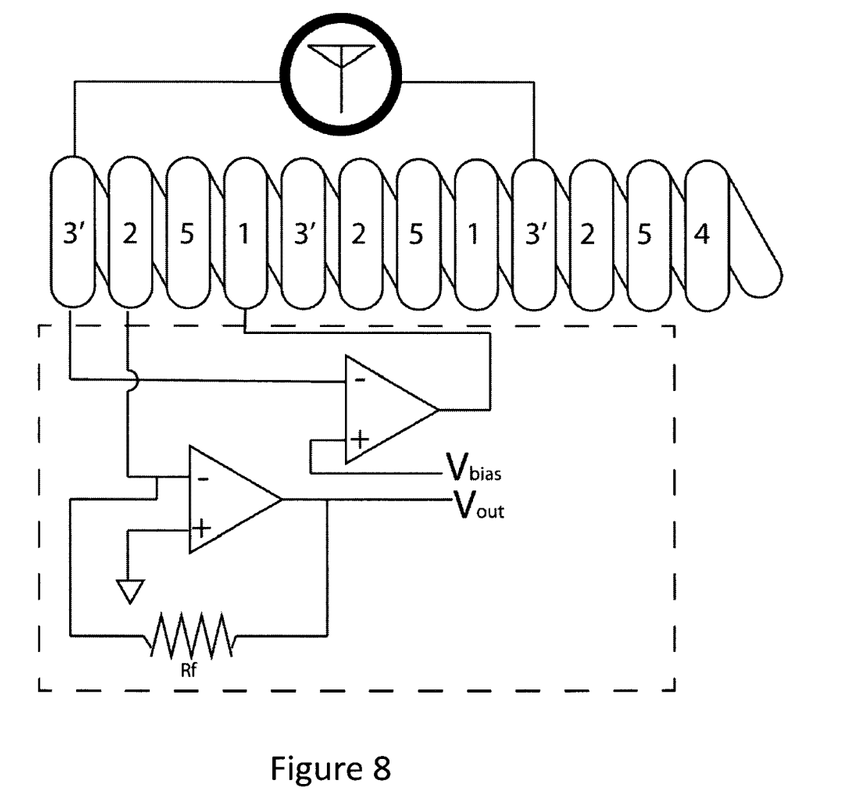

In FIG. 8, the coil consists of four wires coiled in parallel. The wires are connected to the respective points of the electronic circuit component so that they respectively function as: counter electrode 1, working electrode 2, reference electrode 3' and spacer 5. In this embodiment, the wire which functions as a reference electrode 3' also functions as an antenna.

EXAMPLES

Example 1

Preparation of a Pt Working Electrode with an Electroconductive Layer of PEDOT, without a Top Layer (Non-Parallel Wires)

An (enzyme) working electrode was prepared by dispersing 3,4-ethylenedioxythiophene (EDOT) (~$10^{-2}$ M) in phosphate buffered saline (PBS), GOX (~110 U/mL) was added and was allowed to dissolve without agitation.

A three electrode electrochemical system was used whereby a platinum coiled wire (0.01 mm diameter) functions as the working electrode (WE), a platinum coiled wire functions as the counter electrode (CE) and a coiled Ag/AgCl/saturated KCl functions as the reference electrode (RE). The wires were not coiled in parallel, but existed as separate components. The electrodes formed an electrochemical cell for an electropolymerisation process.

The WE was ultrasonically cleaned in ultra-pure water before use. The electrodes were placed in the EDOT/GOx/PBS solution and the potential was cycled between 0.2 and 1.2V/s for 15 cycles. The resulting coated electrode was washed with fresh PBS solution and could be used directly resulting in an immobilized GOx PEDOT matrix onto the platinum wire (Pt/PEDOT/GOx).

Example 2

Sensing Function

A glucose calibration curve was made using the three electrode setup obtained by Example 1.

Glucose PBS solutions from 0.00 to 0.40 mM with steps of 0.05 mM and from 0.50 to 8.00 mM with steps of 0.5 mM were prepared.

Amperometry was performed for the different solutions. One potential step of 600 mV vs Ag/AgCl/saturated KCl was applied and the current was measured for 600 s, while the solution was stirred continuously. The average current and the standard deviation between 60 and 600 seconds was calculated and plotted against the glucose concentration.

Figure 9:
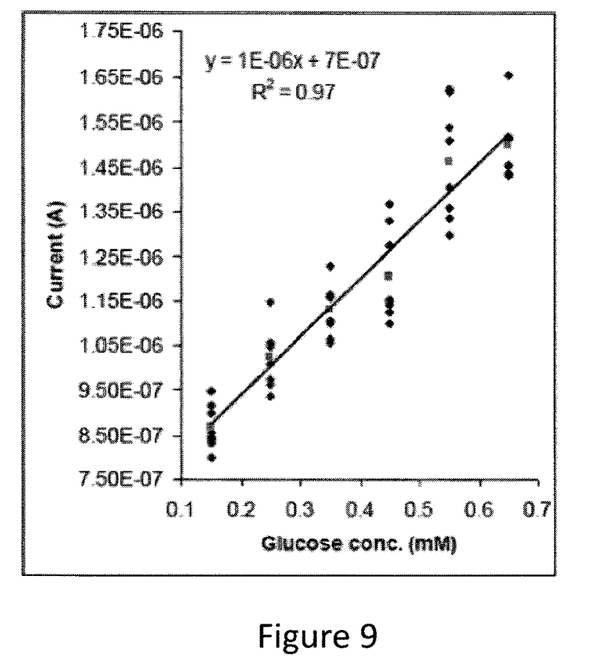
FIGS. 9-12 show various graphs obtained by experiments relating to the invention.
Figure 10:
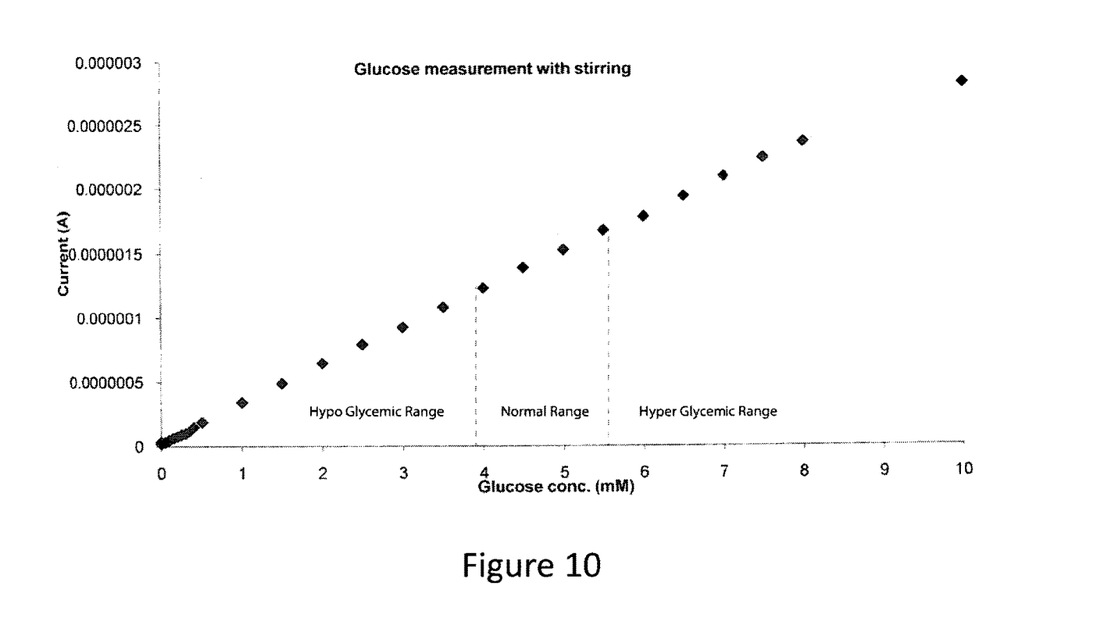

It was observed that the current was linearly proportional to the glucose concentration in a range between 0 and 10 mM. The calibration curve produced for the low concentration range (0 to 0.7 mM) is shown in FIG. 9. Symbols represent individual measurement points and the straight line represents the least squares fit to these points. Additional examples demonstrating the detection of glucose at hyperglycemic, physiological and hypoglycemic concentrations are shown in FIG. 10. The region between 0 mM and 3.9 mM represents the hypoglycemic region, the region between 3.9 mM and 5.5 mM represents the normal glucose region and the region above 5.5 mM represents the hyperglycemic region.

Example 3

Preparation of Pt Working Electrode with a Non-Electroconductive Layer of L-DOPA, without a Top Layer (Non-Parallel Wires)

An (enzyme) working electrode was prepared by dissolving 3,4-dihydroxy-L-phenylalanine (L-DOPA) (20 mg) in 10 mL of a TRIS buffered solution (pH 7.5). A coiled platinum wire was immersed in this solution at room temperature for a period of 17 hours. The L-DOPA coated electrodes were subsequently immersed in a solution of PBS containing ~1000 U/mL of GOx for a period of 4.5 hours.

A coiled platinum wire coated with a non-conductive coating of L-DOPA comprising GOx was thus obtained.

Example 4

Sensing Function

Example 2 was repeated, but the working electrode was replaced by the electrode obtained by example 3. Calibration curves were produced showing that the measured current through the working electrode was substantially proportional to the glucose concentration.

Example 5

Preparation of Pt Working Electrode with a Non-Electroconductive Layer of Chitosan, without a Top Layer (Non-Parallel Wires)

An (enzyme) working electrode was prepared by, dissolving chitosan (~1 g) in 100 mL of 1% acetic acid. The solution was allowed to stand with stirring for a period of 3 hours at room temperature and then stored at 4° C. until required. To a solution of modified chitosan (3 mL) was added 15 μL poly(allylamine) (PAA) molecular weight ~65000 as a 20 wt % solution in $H_2O$. Following complete dissolution of the PAA in the chitosan solution gluteraldehyde (60 μL) was added as a 25 wt % solution in $H_2O$. This solution is subsequently termed solution 1. Into a separate solution of modified chitosan (3 mL) was added GOx (~7 mg) after full dissolution of the GOx in the chitosan solution gluteraldehyde (60 μL) was added as a 25 wt % solution in $H_2O$. This solution is subsequently termed solution 2. A platinum coil cleaned using a mixture of $H_2SO_4$ and $H_2O_2$ rinsed with ultrapure water and further cleaned in an ultrasonic bath containing ultrapure water. The cleaned platinum coil was dip coated with solution 1 and allowed to dry for 2 hours at room temperature before being dipcoated with solution 2 and allowed to dry.

A coiled platinum wire coated with a non-conductive coating of chitosan comprising GOx was thus obtained.

Example 6

Sensing Function

Representative amperometry measurements were carried out by combining the working electrode obtained by Example 5 with a platinum coiled wire counter electrode and a coiled wire Ag/AgCl reference electrode. The coated electrodes were stored in PBS at 4° C. until required.

Figure 11:
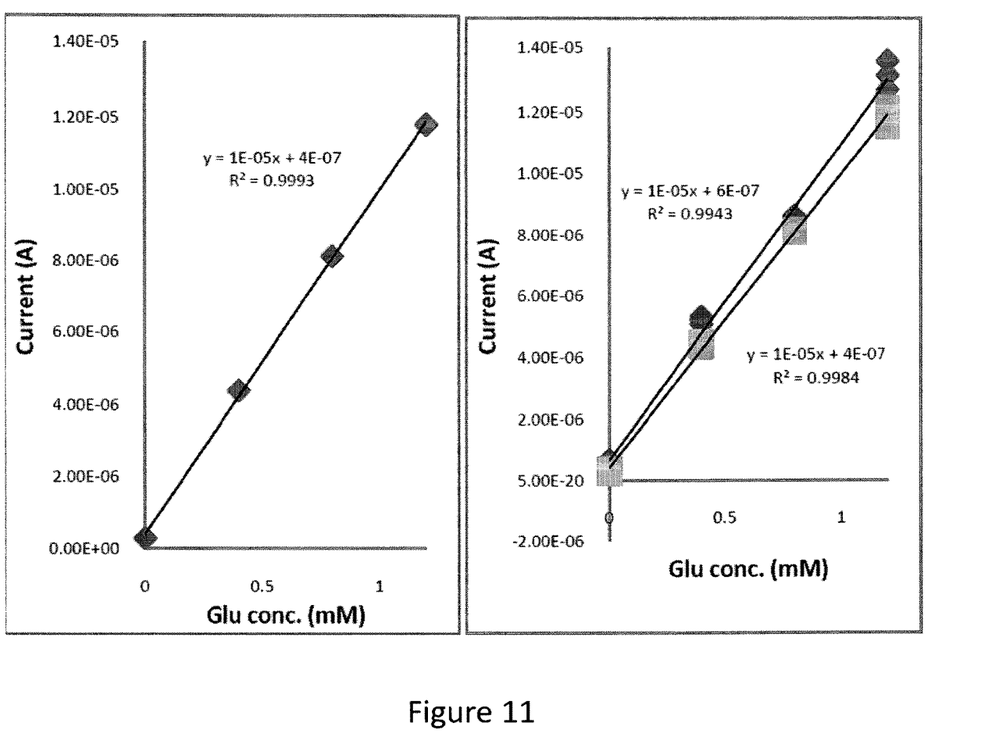

Calibration curves were produced according to the procedure similar to Example 2. The calibration curves produced using this electrode are shown in FIG. 11. The graph on the left represents the current dependence on glucose concentration on day 1 and the graph on left shows the current dependence on glucose concentration on day 2 and day 3.

The measured current through the working electrode was substantially proportional to the glucose concentration.

Example 7

Preparation of Pt Working Electrode with a Non-Electroconductive Layer of Nafion, without a Top Layer (Non-Parallel Wires)

An (enzyme) working electrode was prepared by dissolving GOx (2.7 mg) and bovine serum albumin (BSA) in a solution of PBS (1 mM) containing PEG (615 mg). On full dissolution of the GOx and BSA a solution of gluteraldehyde (15 μL of 2.5 wt % in $H_2O$) was added and the solution was mixed thoroughly. A platinum coiled wire (diameter 0.1 mm) was polished with silica and cleaned in a $H_2SO_4/H_2O_2$ solution (1:3) and rinsed with ultrapure water. The Gox solution (2 μL) was drop cast onto the surface of the cleaned platinum wire and allowed to dry at room temperature for 1 hour. Following drying a solution of Nafion (tetrafluoroethylene-perfluoro-3,6-dioxa-4-methyl-7-octenesulfonic acid copolymer) (10 wt % in water) was placed on the surface and allowed to dry for 1 hour at room temperature.

A coiled platinum wire coated with a non-conductive coating of Nafion comprising GOx was thus obtained.

Example 8

Sensing Function

Example 2 was repeated, but the working electrode was replaced by the electrode obtained by example 7. Calibration curves were produced showing that the measured current through the working electrode was substantially proportional to the glucose concentration.

Example 9

Preparation of a Pt Working Electrode with an Electroconductive Layer of PEDOT without a Top Layer (Non-Parallel Wires)

An (enzyme) working electrode was prepared by, dispersing 3,4-ethylenedioxythiophene (EDOT) (0.01M) in phosphate buffered saline (PBS) containing PEG8000 (0.001M). To the EDOT solution was added GOx (5312.7 U) which was allowed to dissolve without agitation.

A three-electrode electrochemical system was used: consisting of coiled working electrode (WE), diameter 1.5 mm, a coiled platinum wire as counter electrode (CE) and a Ag/AgCl/saturated KCl reference electrode (RE). The electrodes formed an electrochemical cell for an electropolymerisation process.

The WE was precleaned by sequential washing in $H_2SO_4$, ultrapure water and finally in PBS. The electrodes were placed in the EDOT/GOx/PEG/PBS solution and the potential was cycled from 0.3V between 0.2-1.2 V at a scan rate of 0.1 V/s for 30 cycles.

A coiled platinum wire coated with a conductive coating of PEDOT comprising GOx was thus obtained.

Example 10

Sensing Function

Figure 12:
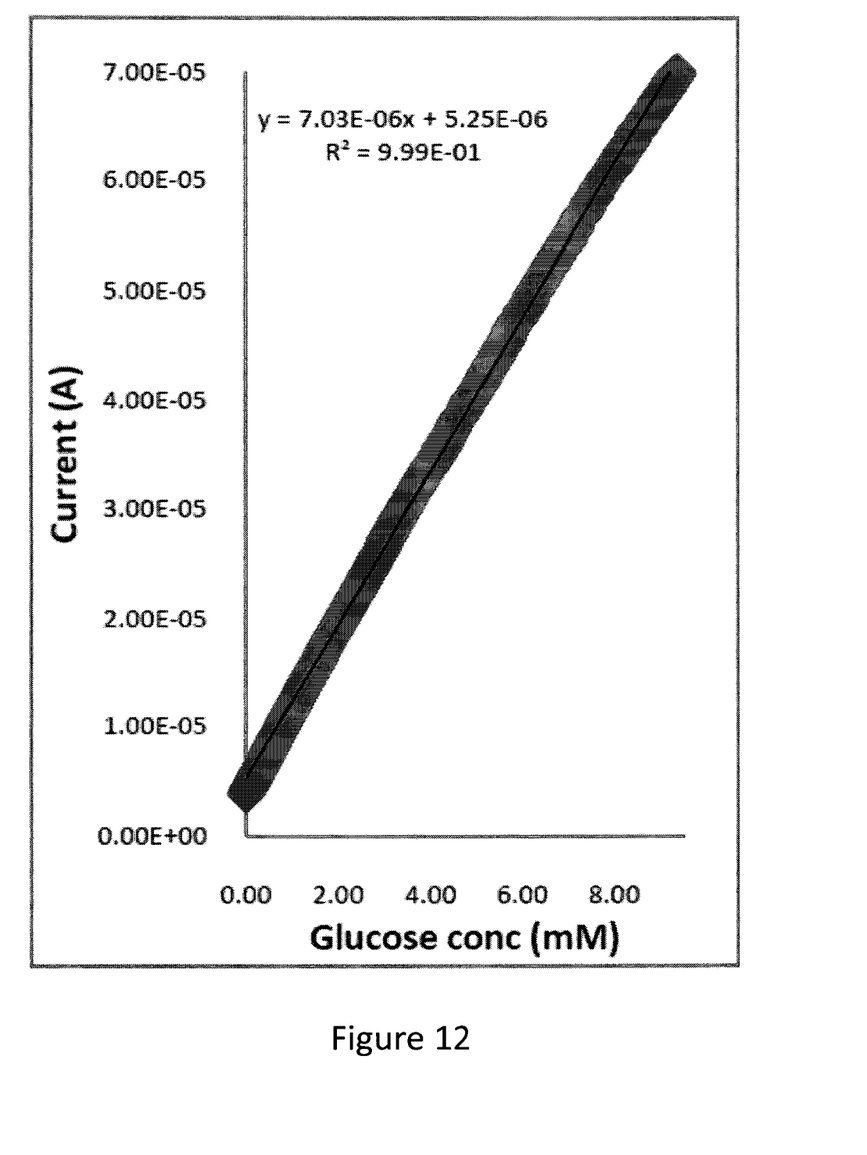

Example 2 was repeated, but the working electrode was replaced by the electrode obtained by example 9. Calibration curves were produced showing that the measured current through the working electrode was substantially proportional to the glucose concentration, as shown in FIG. 12.

Example 11

Parallel Wires

Examples 1-10 are repeated, except that the wires used as the WE, CE and RE are coiled in parallel. No substantial difference is noted in the sensing behavior between the examples wherein the wires not coiled in parallel are used (Examples 1-10) and the examples wherein the wires coiled in parallel are used (Example 11).

Example 12

Parallel Wires with a Top Layer

Examples 1-10 are repeated, except that the wires used as the WE, CE and RE are coiled in parallel and the coil is dip coated with a solution of Nafion (tetrafluoroethylene-perfluoro-3,6-dioxa-4-methyl-7-octenesulfonic acid copolymer) (10 wt % in water) and allowed to dry at room temperature. A coil encapsulated in Nafion is obtained. No substantial difference is noted in the sensing behavior between Examples 11 and 12.

Example 13

Preparation of a Pt Working Electrode with an Electroconductive Layer of PEDOT (Parallel Wires)

A wire of platinum plated stainless steel, diameter 0.152 mm, may be coated with a copolymer of BMA and NVP. Another wire of platinum plated stainless steel, diameter 0.152 mm, may be coated electrochemically with PEDOT/GOx which again may be coated with the copolymer of BMA and NVP. A silver plated stainless steel wire, diameter 0.152 mm, may be coated with a silverchloride layer which may also be coated with the copolymer. These three wires may be coiled in parallel around a mandrel. The formed coil then have an outer diameter of 0.87 mm. After removal of the mandrel the coil may be cut into pieces of 1 cm in length. One of the ends of the coil may be closed with a drop of UV-curable polymer. The three wires at the other end of the coil may then be connected to an electronic circuit.

Calibration curves are produced according to the procedure similar to Example 2. The measured current through the working electrode is substantially proportional to the glucose concentration.

Example 14

The coil made according to the examples 1-13 is connected to an electronic circuit component to form the biosensor. The electronic signal obtained from the sensor may be transmitted by an antenna system and received by an external device, for example mounted in a pair of glasses. This may in turn amplify the signal and transmit it to another device, for example an insulin pump.

What is claimed is:

1. A biosensor adapted for wearing under an eyelid, comprising: a hollow coil comprising wires coiled in parallel such that the biosensor is flexible and can follow a shape of the surrounding environment and an electronic circuit component operably connected to the coil,
   wherein the wires coiled in parallel include at least a first coiled wire which is used as a counter electrode, a second coiled wire which is used as a working electrode and a third coiled wire which is used as a reference electrode,
   wherein the second coiled wire is provided with a biocompatible layer comprising a bioreceptor, wherein the second coiled wire has a Pt surface,
   wherein the electronic circuit component is capable of generating an input signal for a transceiver based upon the activity of the bioreceptor and wirelessly sending the input signal to the transceiver,
   wherein the electronic circuit component is encapsulated in a biocompatible resin,
   wherein the coil and the encapsulated electronic circuit component are encapsulated in a single, continuous top layer of a biocompatible material,
   wherein the biocompatible material is a hydrophilic material, and
   wherein the hydrophilic material is chosen from the group consisting of: a copolymer of a hydrophobic reactive monomer and a hydrophilic reactive monomer; a block co-polymer of polyethers wherein each block differs by at least one carbon in an aliphatic region and a homopolymer of a polysaccharide, and
   wherein the biosensor can monitor glucose levels in lacrimal fluid.

2. The biosensor according to claim 1, wherein the biocompatible layer comprising the bioreceptor is electroconductive.

3. The biosensor according to claim 2, wherein the biocompatible layer comprises an electron conductive polymer synthesised from an optionally substituted five-membered heterocycle of formula (I)

(I)

wherein $R^1$ stands for a hetero atom,
   wherein $R^2$, $R^3$ are each independently selected from the group of: hydrogen, an alkyl that is substituted or unsubstituted, wherein the substituted alkyl is substituted with one or more of a hydroxyl group, alkyl group, and alkyl ether; or an o-alkyl that is substituted or unsubstituted; and wherein $R^2$ and $R^3$ either a) forms a ring together with the carbon atoms to which they are connected or b) does not form a ring together with the carbon atoms to which they are connected.

4. The biosensor according to claim 1, wherein the biocompatible resin is a UV curable medical adhesive.

5. The biosensor according to claim 1, wherein the third coiled wire is a silver/silver chloride reference electrode.

6. The biosensor according to claim 1, wherein the wires further include a fourth coiled wire coated with an insulating layer which may be used as an antenna.

7. The biosensor according to claim 6, wherein the insulating layer is made of parylene; polytetrafluoro ethylene; fluorinated ethylene propylene; perfluroxalkoxy copolymer; polyphenylene sulfide; polyether block amide; polyether ketone; poly amide; polyimide; polyesterimide; polyethylene; polyvinylidene fluoride; or a polyurethane or co-polymers thereof.

8. The biosensor according to claim 1, wherein the wires further include a fifth coiled wire coated with an insulating layer which may be used as a spacer.

9. The biosensor according to claim 1, comprising one or more further coiled wires provided with a biocompatible layer comprising a bioreceptor, which may be used as a further working electrode.

10. The biosensor according to claim 1, wherein the bioreceptor is an oxidoreductase.

11. The biosensor according to claim 1, wherein the bioreceptor is an oxidoreductase of enzyme commission groups EC 1.X.3 where X=1-17.

12. The biosensor according to claim 1, wherein the bioreceptor is chosen from the group consisting of glucose oxidase, lactate dehydrogenase, pyruvate dehydrogenase and pyruvate oxidase.

13. The biosensor according to claim 1, wherein the biosensor has a diameter of 0.1 to 3 mm.

14. The biosensor according to claim 1, wherein the biosensor has a length of 5 to 20 mm.

15. The biosensor according to claim 1, wherein the electronic circuit component is attached at the end of the coil and the other end of the coil is provided with the biocompatible resin.

16. A medical device comprising the biosensor according to claim 1 and a remote receiver.

17. A biosensor adapted for wearing under an eyelid, comprising: a hollow coil comprising wires coiled in parallel such that the biosensor is flexible and can follow a shape of the surrounding environment and an electronic circuit component operably connected to the coil,
- wherein the wires coiled in parallel include at least a first coiled wire which is used as a counter electrode, a second coiled wire which is used as a working electrode and a third coiled wire which is used as a reference electrode,
- wherein the second coiled wire is provided with a biocompatible layer comprising a bioreceptor,
- wherein the electronic circuit component is capable of generating an input signal for a transceiver based upon the activity of the bioreceptor and wirelessly sending the input signal to the transceiver,
- wherein the electronic circuit component is encapsulated in a biocompatible resin,
- wherein the third coiled wire is coated with a silver chloride layer,
- wherein the wires coiled in parallel and the encapsulated electronic circuit component are covered by a single continuous top layer of a second biocompatible material that is hydrophilic, and
- wherein the first coiled wire is in direct contact with the top layer, and wherein the biosensor can monitor glucose levels in lacrimal fluid.

\* \* \* \* \*